US012767973B2

(12) United States Patent
Bidi et al.

(10) Patent No.: US 12,767,973 B2
(45) Date of Patent: Oct. 20, 2026

(54) SOLUTION FOR MEASUREMENT OF TREHALASE IN URINE AND MEASUREMENT METHOD USING THIS SOLUTION

(71) Applicant: Argeron Medikal Arastirma Sanayi Ve Ticaret Anonim Sirketi, Dösemealti (AR)

(72) Inventors: Bülent Bidi, Dösemealti (AR); Abdullah Olgun, Dösemealti (AR)

( * ) Notice: Subject to any disclaimer, the term of this patent is extended or adjusted under 35 U.S.C. 154(b) by 508 days.

(21) Appl. No.: 18/255,810

(22) PCT Filed: Nov. 11, 2021

(86) PCT No.: PCT/TR2021/051187

§ 371 (c)(1), (2) Date: Jun. 2, 2023

(87) PCT Pub. No.: WO2022/146320

PCT Pub. Date: Jul. 7, 2022

(65) Prior Publication Data

US 2024/0102076 A1 Mar. 28, 2024

(51) Int. Cl.

| | |
|---|---|
| ***C12Q 1/34*** | (2006.01) |
| ***C12N 9/24*** | (2006.01) |
| ***G01N 33/573*** | (2006.01) |

(52) U.S. Cl.

CPC ............. *C12Q 1/34* (2013.01); *C12N 9/2402* (2013.01); *C12Y 302/01028* (2013.01)

(58) Field of Classification Search

CPC .................... C12Q 1/34; C12N 9/2402; C12Y 302/01028; G01N 2333/926; G01N 33/573

See application file for complete search history.

(56) References Cited

FOREIGN PATENT DOCUMENTS

| | | | |
|---|---|---|---|
| CN | 111007255 | A | 4/2020 |
| EP | 2839260 | A1 | 2/2015 |
| WO | 2019119148 | A1 | 6/2019 |

OTHER PUBLICATIONS

Nakano et al., “Elevation of Urinary Trehalase and Maltase Activities with Maturity-Onset Diabetes Mellitus”, J. Clin. Biochem. Nutr., 1987, vol. 3, pp. 125-133. (Year: 1987).*

Dahlqvist A., “Assay of Intestinal Disaccharidases”, Analytical Biochemistry, 1968, vol. 22, pp. 99-107. (Year: 1968).*

Kovanci B. et al., “Urinary trehalase activity in contrast-associated acute kidney injury”, European Review for Medical and Pharmacological Sciences, 2023, vol. 27, pp. 1298-1304. (Year: 2023).*

International Search Report and Written Opinion of the International Searching Authority for corresponding PCT/TR2021/051187 dated Apr. 11, 2022.

* cited by examiner

*Primary Examiner* — Satyendra K Singh

(74) *Attorney, Agent, or Firm* — Egbert, McDaniel & Swartz, PLLC

(57) ABSTRACT

A method for measuring trehalase enzyme activity in a urine sample has the steps of mixing a trehalose solution with the urine sample, incubating the mixture, measuring glucose in the incubated mixture, mixing deionized water with the urine sample so as to form a blank mixture, incubating the blank mixture, measuring glucose in the blank mixture, and calculating a difference between the measured glucose in the incubated mixture and the measured glucose in the blank mixture to determine the trehalase enzyme activity.

6 Claims, No Drawings

SOLUTION FOR MEASUREMENT OF TREHALASE IN URINE AND MEASUREMENT METHOD USING THIS SOLUTION

THE FIELD OF THE INVENTION

Invention relates to a trehalose solution for use with urinary glucose measurement kits in in vitro diagnostic (biochemical medical diagnosis) field to measure urinary trehalase enzyme activity as indication of kidney damage, and a measurement method where this solution is used.

BACKGROUND OF THE INVENTION

Trehalase is a glycoprotein structured enzyme of 75 kDa molecular weight and present in renal proximal tubules and intestines. Urinary trehalase measurement can be used for screening, diagnosis and monitoring of damage occurred in renal proximal tubules[(1,2)]. It is reported that trehalase activity was higher than the control group even when proteinuria and glucosuria are negative from the early stages of diabetes; and in late stages of diabetes, activity decreases because of disappearance of brush borders in proximal tubules[(3)]. It can show early kidney damage due to some environmental toxins. It was shown that trehalase activity was increased in comparison to control group in workers who melt lead; there was a positive linear relationship between blood lead level and urinary trehalase activity. And in case of environmental cadmium exposure, a similar increase in activity was seen[(4-6)]. It was reported that the use of ampicillin and tobramycin antibiotics in infants increased urinary trehalase activity[(7)]. In chronic glomerular disease and particularly nephrotic syndrome, urinary trehalase activity increase was observed[(8)].

At present there are various methods used for measurement of trehalase in urine. These methods are divided into two main groups, namely, those measuring trehalase enzyme activity (colorimetric) and mass measuring ones (immunochemical). However, there is no example developed as a kit commonly used in routine diagnostic laboratories. For that reason, methods are needed particularly to provide early, fast, widespread and economical diagnosis of kidney damage.

As a result, due to above described disadvantages and inadequacy of existing solutions it has been necessary to make development in the related art.

BRIEF DESCRIPTION OF THE INVENTION

The present invention relates to urinary trehalase measurement meeting the needs mentioned above, eliminating all disadvantages and providing some additional advantages.

Primary purpose of invention is to provide the use of kits already used for measurement of urinary glucose for urinary trehalase activity measurement also and thus allow very fast and widely satisfaction of need for trehalase measurement. Because contrary to urinary trehalase measurement, urinary glucose measurement is a routine measurement made in almost all medical diagnostic laboratories all around the world. The invention will enable the use of widely used urinary glucose measurements for urinary trehalase activity measurement also. There is no other product used for this purpose.

In order to achieve above mentioned purposes, the invention is a trehalose solution for use together with urinary glucose measurement kits for the measurement of urinary trehalase enzyme activity in biochemical diagnostic field. In a preferred application of the invention, said solution contains trehalose in a concentration range of 0.2-68.0 g/dL, preferably 40 g/dL. The invention also comprises urinary trehalase measurement kits containing said solution.

In order to achieve above mentioned purposes, the invention is a urinary trehalase enzyme measurement method wherein said solution is used and comprises following process steps:

a) Mixing trehalose solution and urine sample,
b) Incubating mixture at a predetermined temperature and duration,
c) Measurement of glucose in the mixture by glucose measurement kit using the selected urine,
d) Measurement of glucose in de-ionized water added urine mixture at said equivalent conditions in previous steps,
e) Evaluation of difference between two glucose measurement results.

According to an application of the invention, said trehalose solution in process step "a" contains trehalose in a concentration range of 0.2-68.9 g/dL, preferably 40 g/dL.

According to an application of the invention, in process step "a" 1 unit volume of trehalose solution is mixed with 39 unit volume of urine.

According to an application of the invention, in process step "d" 1 unit volume of de-ionized water is mixed with 39 unit volume of urine.

According to an application of the invention, in process step "e", trehalose solution and de-ionized water are mixed and the difference between these two different urinary glucose measurements is calculated as trehalase activity.

According to an application of the invention, in process step "e", from the concentration of glucose formed by Trehalase enzyme, trehalase activity result is calculated as U/L.

According to an application of invention, in process step "e", Trehalase activity producing 2 μmol glucose from 1 μmol trehalose per minute is assumed as Unit (U).

The structural and characteristic features of the invention and all advantages will be understood better in detailed descriptions given below and therefore, the assessment should be made taking into account the figures and detailed explanations.

DETAILED DESCRIPTION OF THE INVENTION

In this detailed description, the invention and preferred applications of the invention have been described for the purpose of better understanding of the matter and in a manner not forming any restrictive effect.

The invention is a trehalose solution for use together with urinary glucose measurement kits for measurement of urinary trehalase enzyme activity in biochemical diagnostic field.

Trehalose solution of the invention provides use of kits used for urinary glucose measurement routinely at medical diagnostic laboratories worldwide for urinary trehalase activity measurement too.

Trehalose contained in solution of the invention is added to urine. It is transformed into glucose by trehalase enzyme in urine.

The kit used for measurement of glucose in urine routinely can also measure glucose in urine having been added solution of the invention or deionized water. The difference between two different measurements with solution and deionized water added shows trehalase activity.

Urinary glucose measurement kits used under the invention also contains urinary analysis reactive dipsticks. It measures glucose formed in urine treated with trehalose solution of the invention. Any type of commercial kits used routinely at medical diagnostic laboratories can be used for measurement of glucose in urine by solution of the invention.

Method for measurement of trehalase enzyme in urine performed by solution of the invention comprises following processes steps in the most basic form.

- Mixing trehalose solution and urine sample,
- Incubating mixture at predetermined temperature and duration,
- Measurement of glucose in mixture by glucose measurement kit with selected urine,
- Measurement of glucose in de-ionized water added urine mixture at said equivalent conditions in previous steps,
- Evaluation of difference glucose results between two measurements.

Trehalose solution of the invention contains trehalose in 0.2-68.9 g/dL concentration range, at preferably 40 g/dL dissolved in deionized water or another solution in a manner not to affect trehalase activity. 1 unit volume of this solution is mixed with 39 units volume urine. In other applications of the invention, if trehalose solution contains trehalose at a concentration different from 40 g/dL, solution and urine volumes are changed to contain trehalose at a final concentration of preferably 1 g/dL in 0.1-5 g/dL range. It is kept at an appropriate temperature for an appropriate time. Trehalose of the solution is converted into glucose by trehalase enzyme in urine. The higher the trehalase in concentration in urine the more the glucose is produced.

The kit used for measurement of glucose in urine routinely can also measure glucose in urine having been added solution of the invention.

Same measurement is also made by use of deionized water added urine of same volume instead of solution and incubated at the same conditions (time and temperature). Result of this measurement is assumed as blank.

The difference between two different urine glucose measurements by solution and deionized water added shows trehalase activity.

From glucose concentration formed by Trehalase enzyme, trehalase activity result is calculated in U/L. In the calculation the time period when solution is incubated by urine, dilution factor and final incubation volume are also taken into account. Trehalase activity producing 2 μmol glucose from 1 μmol trehalose per minute is assumed as one Unit (U).

Urine Trehalase Activity Measurement Example 1:

Collection of Urine Sample:

A random midstream urine was collected from patient. Urine sample should not be cloudy. The urine sample was put into a clean and dry tube. In alternative applications, the samples not to be analyzed immediately and can be stored for 2 hours at +4° C. and 48 hours at −20° C. in closed tubes.

Mixture and Incubation of Urine and 40% Trehalose Solution:

975 μL urine taken from patient and 25 μL 40% trehalose solution were put into Sample tube. 975 μL urine taken from patient and 25 μL deionized water were put into blank tube. Tubes were incubated at 37° C. for 30 minutes.

In alternative applications, if trehalose solution is of different concentration, volumes of used urine and solution can be changed accordingly. Incubation period and temperature may vary subject to laboratory conditions.

Trehalase Activity Measurement:

Measurement principle is based on measurement of glucose formed by conversion of trehalose in urine into glucose by trehalase enzyme.

Urine glucose was measured by glucose kit of ARCHITECT brand (Reference no: 3L82, Germany) at Abbot Architect C8000 (USA) device by kinetic colorimetric method according to kit instructions.

Glucose was measured separately in trehalose solution added urine and deionized water added urine samples and the difference was accepted as trehalase activity.

Principle of Urinary Glucose Measurement Experiment:

Glucose is phosphorylated by hexokinasein presence of adenosine triphosphate (ATP) and magnesium ions; and glucose-6-phosphate (G-6-P) and adenosine diphosphate (ADP) occurs. While glucose 6 phosphate-dehydrogenase (G-6-PDH) oxidizes G-6-P to phosphogluconate, nicotinamide adenine dinucleotide (NAD) is converted to reduced nicotinamide adenine dinucleotide (NADH). One NADH is produced per each consumed glucose molecule. Produced NADH absorbs light at 340 nm and is detected spectrophotometrically as increased absorbance. Method is linear up to <800 mg/dL (44 mmol/L).

Calculation of Urinary Trehalase Activity:

After separate glucose measurements with trehalose solution added urine and deionized water added urine samples, following results were obtained:

Glucose concentration of Trehalose solution added urine: 115 mg/dL

Glucose concentration of deionized water added urine: 7 mg/dL

Difference=115 mg/dL=7 mg/dL=108 mg/dL=1080 mg/L=6 mM=6000 μM (Note: Molecular weight of glucose is 180 g/mol)

Trehalase activity producing 2 μmol glucose from 1 μmol trehalose per minute is assumed as one Unit (U). Since incubation time of experiment is 30 minutes, glucose produced in 1 minute:

6000 μM/30 min.=200 μM/min./2=100 U/L

Since trehalose solution was added in 1 unit volume into 39 units volume of urine before measurement, the result is multiplied by "40÷39=1.025" to correct dilution factor:

Urinary trehalase activity: 100 U/L×1.025

Urinary trehalase activity: 102.5 U/L

REFERENCES

1. Ishihara R, Taketani S, Sasai-Takedatsu M, Adachi Y, Kino M, Furuya A, et al. *ELISA for urinary trehalase with monoclonal antibodies: A technique for assessment of tubular damage. din Chem.* 2000;
2. M. S-T, S. T, N. N, T. F, R. T, T. K. *Human trehalase: Characterization, localization, and its increase in urine by renal proximal tubular damage. Nephron.* 1996.
3. NAKANO M, IGUCHI A, KURIMOTO H, SAKAMOTO N. *Elevation of Urinary Trehalase and Maltase Activities with Maturity-Onset Diabetes Mellitus. J din Biochem Nutr.* 2011;
4. Skoczyliska A, Martynowicz H, Poreba R, Antonowicz-Juchniewicz J, Sieradzki A, Andrzejak R. *Urinary trehalase activity as an indicator of renal dysfunction in lead smelters. Med Pr.* 2001;
5. Nakano M, Aoshima K, Katoh T, Teranishi H, Kasuya M. *Urinary trehalase activity and renal brush-border dam-*

*age in inhabitants of a cadmium-polluted area* (*Jinzu River basin*). *Toxicol Lett.* 1986;

6. Iwata K, Katoh T, Morikawa Y, Aoshima K, Nishijo M, Teranishi H, et al. *Urinary trehalase activity as an indicator of kidney injury due to environmental cadmium exposure. Arch Toxicol.* 1988;
7. Sasai-Takedatsu M, Kojima T, Taketani S, Ono A, Kitamura N, Kobayashi Y. *Urinary Trehalase Activity Is a Useful Marker of Renal Proximal Tubular Damage in Newborn Infants. Nephron.* 1995;
8. Niwa T, Katsuzak T, Yazawa T, Tatemichi N, Emoto Y, Miyazaki T, et al. *Urinary Trehalase Activity in Chronic Glomerulonephritis. Nephron.* 1993;

The invention claimed is:

1. A method for measuring trehalase enzyme activity in a urine sample, the method comprising:

mixing a trehalose solution dissolved in deionized water with the urine sample;

incubating the mixture of the trehalose solution and the urine sample at a predetermined temperature and duration;

measuring glucose in the incubated mixture by using a glucose measurement kit;

mixing a deionized water with the urine sample so as to form a blank mixture;

incubating the blank mixture under the predetermined temperature and duration as in the step of incubating the mixture;

measuring glucose in the blank mixture by using the glucose measurement kit; and calculating a difference between the measured glucose in the incubated mixture and the measured glucose in the blank mixture to determine the trehalase enzyme activity.

2. The method of claim 1, wherein the trehalose solution in the step of mixing the trehalose solution and the urine sample has trehalose at a concentration of 40 g/dL.

3. The method of claim 1, wherein in the step of mixing the trehalose solution and the urine sample, one unit volume of the trehalose solution is mixed with thirty-nine unit volumes of the urine sample.

4. The method of claim 1, wherein in the step of mixing the deionized water with the urine sample, one unit volume of the deionized water is mixed with the thirty-nine unit volumes of the urine sample.

5. The method of claim 1, wherein the step of determining trehalase activity is calculated by subtracting a measured glucose concentration of the blank mixture from a measured glucose concentration of the incubated mixture and measured as units per liter.

6. The method of claim 5, wherein one unit is defined as trehalase activity that produces two μmol of glucose from one μmol of trehalose per minute.

* * * * *